United States Patent
Hissong et al.

(10) Patent No.: US 10,279,072 B2
(45) Date of Patent: *May 7, 2019

(54) ARTIFICIAL SCAB FOR USE IN AN AIRWAY

(71) Applicant: Medtronic, Inc., Minneapolis, MN (US)

(72) Inventors: James B. Hissong, Jacksonville, FL (US); Matthew F. Myntti, St. Augustine, FL (US); Jennifer G. Medina, Jacksonville, FL (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/645,674

(22) Filed: Jul. 10, 2017

(65) Prior Publication Data
US 2017/0304487 A1 Oct. 26, 2017

Related U.S. Application Data

(62) Division of application No. 13/282,332, filed on Oct. 26, 2011, now Pat. No. 9,700,648.
(Continued)

(51) Int. Cl.
*A61L 24/04* (2006.01)
*C08L 5/00* (2006.01)
(Continued)

(52) U.S. Cl.
CPC ......... *A61L 24/043* (2013.01); *A61L 26/0052* (2013.01); *C08L 1/00* (2013.01);
(Continued)

(58) Field of Classification Search
None
See application file for complete search history.

(56) References Cited

U.S. PATENT DOCUMENTS 2,772,999 A * 12/1956 Masci ............... A61L 15/28
424/445
4,952,618 A 8/1990 Olsen
(Continued)

FOREIGN PATENT DOCUMENTS

JP 2003-321398 11/2003
WO WO 1998/022114 A1 5/1998
(Continued)

OTHER PUBLICATIONS

Parent U.S. Appl. No. 13/282,332, now U.S. Pat. No. 9,700,648 issued on Jul. 11, 2017.
(Continued)

*Primary Examiner* — Bethany P Barham
*Assistant Examiner* — Dominic Lazaro
(74) *Attorney, Agent, or Firm* — Patterson Thuente Pedersen, P.A.

(57) ABSTRACT

Body tissue and structures in an airway may be treated with an artificial scab comprising an inhomogeneous, uncohesive, solid sheet-like body comprising a granular mixture of chitosan and polysaccharide particles. The artificial scab breaks apart into smaller pieces if peeled away from the surgical site or wound, thus reducing the risk of airway occlusion.

18 Claims, 1 Drawing Sheet

Related U.S. Application Data

(60) Provisional application No. 61/407,391, filed on Oct. 27, 2010.

(51) Int. Cl.
    *C08L 3/04*     (2006.01)
    *A61L 26/00*    (2006.01)
    *C08L 1/00*     (2006.01)
    *C08L 5/08*     (2006.01)
    *C08L 3/10*     (2006.01)

(52) U.S. Cl.
    CPC .................. *C08L 3/04* (2013.01); *C08L 3/10* (2013.01); *C08L 5/00* (2013.01); *C08L 5/08* (2013.01); *A61L 2300/00* (2013.01)

(56) References Cited

U.S. PATENT DOCUMENTS

| | | | |
|---|---|---|---|
| 5,484,913 A | 1/1996 | Stilwell et al. | |
| 7,727,547 B2 | 6/2010 | Fortune et al. | |
| 7,834,065 B2 | 11/2010 | Nakajima et al. | |
| 8,088,095 B2 | 1/2012 | Hissong et al. | |
| 8,802,652 B2 | 8/2014 | Myntti et al. | |
| 9,119,896 B2 | 9/2015 | Hissong et al. | |
| 2002/0037329 A1 | 3/2002 | Martis | |
| 2002/0106409 A1 | 8/2002 | Sawhney et al. | |
| 2003/0135208 A1* | 7/2003 | Luigi | A61B 18/1485 606/49 |
| 2004/0052850 A1 | 3/2004 | Schankereli | |
| 2005/0002893 A1 | 1/2005 | Goldmann | |
| 2006/0172000 A1* | 8/2006 | Cullen | A61L 15/225 424/445 |
| 2007/0066924 A1 | 3/2007 | Hopman et al. | |
| 2007/0264310 A1 | 11/2007 | Hissong et al. | |
| 2008/0195037 A1 | 8/2008 | Hissong et al. | |
| 2008/0319101 A1 | 12/2008 | Nakajima | |
| 2009/0062233 A1* | 3/2009 | Ji | A61K 31/718 514/60 |
| 2009/0270346 A1 | 10/2009 | Tijsma et al. | |
| 2009/0291911 A1 | 11/2009 | Myntti et al. | |
| 2009/0291912 A1 | 11/2009 | Tijsma et al. | |

FOREIGN PATENT DOCUMENTS

| | | | |
|---|---|---|---|
| WO | WO-9822114 A1 * | 5/1998 | ........... A61K 9/1623 |
| WO | WO 03/020771 A1 | 3/2003 | |
| WO | WO 2004/026200 A2 | 5/2006 | |
| WO | WO 2009/132225 A2 | 10/2009 | |
| WO | WO 2009/132228 A1 | 10/2009 | |
| WO | WO 2009/132229 A2 | 10/2009 | |

OTHER PUBLICATIONS

PCT/US2011/057893 International Report on Patentability dated Feb. 5, 2013, 17 pages.

Gross et al., Autologous Fibrin Sealant Reduces Pain After Tonsillectomy, Laryngoscope, 111: pp. 259-263 (Feb. 2001).

Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004).

Krauland et al., *Viscoelastic Properties of a New in situ Gelling Thiolated Chitosan Conjugate*, Drug Development and Industrial Pharmacy, 31, 885-893 (2005).

Bernkop-Schnürch, *Thiomers: A new generation of mucoadhesive polymers*, Advanced Drug Delivery Reviews, 57, 1569-1582 (2005).

Bernkop-Schnürch, A., et al., "*Improvement in the mucoadhesive properties of alginate by the covalent attachment of cysteine*", Journal of Controlled Release, Elsevier, 71, 277-285 (2001).

Bernkop-Schnürch et al., *Thiomers: Preparation and in vitro evaluation of a mucoadhesive nanoparticulate drug delivery system*, International journal of Pharmaceutics, 317, 76-81 (2006).

Weng et al., *Rheological Characterization of in Situ Crosslinkable Hydrogels Formulated from Oxidized Dextran and N-Carboxyethyl Chitosan*, Biomacromolecules, 8, 1109-1115 (2007).

Senel et al., *Potential application of chitosan in veterinary medicine*, Science Direct, Advanced Drug Delivery Reviews 56, pp. 1467-1480 (2004).

Wen-Yi et al., "In situ copolymerization and compatibilization of polyester and polystryrene blends. II. Thermally and chemically induced reaction and mechanical properties", Polymer 42, pp. 5121-5134 (2001).

* cited by examiner

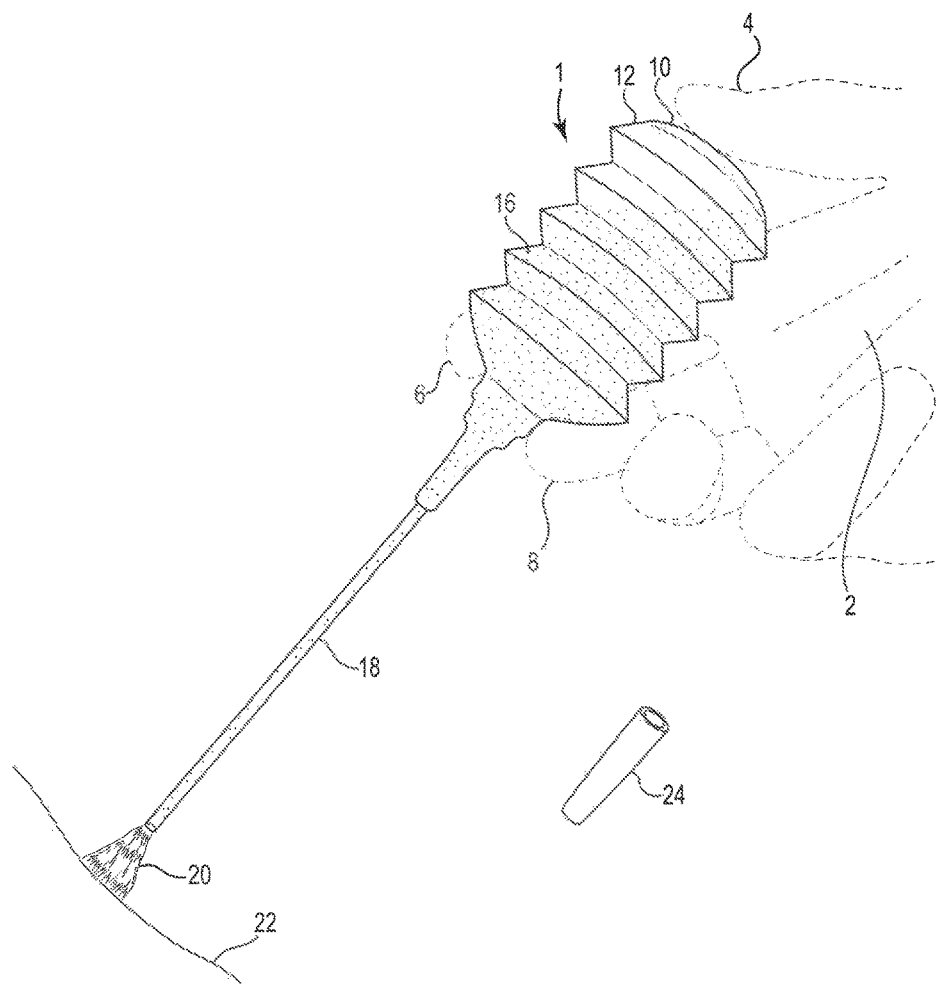

ARTIFICIAL SCAB FOR USE IN AN AIRWAY

CROSS-REFERENCE TO RELATED APPLICATION

This application is a divisional of U.S. patent application Ser. No. 13/282,332 filed Oct. 26, 2011, now allowed, which claims the benefit of U.S. Provisional Application Ser. No. 61/407,391 filed Oct. 27, 2010, and entitled "ARTIFICIAL SCAB FOR USE IN AN AIRWAY", the disclosures of each of which are incorporated herein by reference.

FIELD OF THE INVENTION

This invention relates to materials for use in treating wounds and surgical sites in the throat, nasal passages and elsewhere in the respiratory tract.

BACKGROUND

Adenoids (pharyngeal tonsils) and tonsils (palatine tonsils) are involved in a number of diseases of the ear, nose, and throat including chronic otitis media with effusion (COME), recurrent acute otitis media (RAOM), adenoiditis, pediatric chronic sinusitis, tonsillitis, pediatric obstructive sleep apnea (OSA), adult OSA, and chronic strep throat. Lingual tonsils can become infected and may cause or aggravate sore throat pain. Initial treatment for these various conditions normally involves administration of oral medications or, in the case of pediatric and adult sleep apnea, use of a continuous positive airway pressure (CPAP) device. Otitis media may be treated using ventilation tube surgery. Treatment success rates are often less than optimal, and in many cases the tonsils, adenoids or other throat tissue eventually may be surgically removed. Such surgeries are however painful, typically require the administration of anesthetics and lengthy post-operative recovery periods, and may be accompanied by complications such as post-operative bleeding, dehydration, weight loss, peritonsillar abscess, torticilis (neck stiffness), tissue regrowth, repeat surgery to address incomplete prior tissue removal, continued COME or RAOM, continued OSA, and occasionally death. Existing post-surgical treatments generally provide only limited relief, and may include dietary limitations, rinses, and administration of painkilling medications or oral antibiotics to reduce post-operative pain and infections.

SUMMARY OF THE INVENTION

U.S. Patent Application No. US 2008/0195037 A1 describes a polymeric film-forming sealant. U.S. Patent Application No. US 2009/0270346 A1 describes a two-part fluid composition made from chitosan and oxidized polysaccharide. U.S. Patent Application No. US 2009/0291912 A1 describes a sprayable two-part fluid composition made from a partially crosslinked polysaccharide and a further crosslinker for the polysaccharide, wherein the polysaccharide or further crosslinker comprise chitosan and the composition when hydrated and mixed can be delivered as a fluid through a spray applicator to provide a thin, conformal protective layer on a body temperature substantially vertical skin surface. In general, the goal in these three patent applications (all of which are assigned to the assignee of the present invention) is the formation of a homogenous, cohesive protective hydrogel layer or a homogeneous, cohesive protective barrier film at the treatment site. Although useful for many types of surgery, such a hydrogel layer or barrier film may, when applied in an airway, cause accidental airway obstruction and choking or other hazards if the hydrogel layer or barrier film falls off or otherwise becomes dislodged from the treatment site. Similar problems may arise when using other film-forming wound dressings including cyanoacrylates.

The present invention provides, in one aspect, a composition comprising a substantially dry, free-flowing powdered mixture of at least partially solvatable chitosan particles and at least partially solvatable oxidized polysaccharide particles, which mixture adheres to a surgical site or wound moistened with bodily fluids and thereby forms an inhomogeneous, uncohesive, solid sheet-like body that breaks apart into smaller pieces if peeled away from the surgical site or wound.

The invention provides in another aspect an artificial scab comprising an inhomogeneous, uncohesive, solid sheet-like body adhered to a surgical site or wound, the body comprising a granular mixture of chitosan and polysaccharide particles that breaks apart into smaller pieces when peeled away from the surgical site or wound.

The invention provides in yet another aspect a method comprising:
 a) applying a substantially dry, free-flowing powdered mixture of at least partially solvatable chitosan particles and at least partially solvatable oxidized polysaccharide particles to a surgical site or wound in an airway moistened with blood, other bodily fluids or water; and
 b) forming an artificial scab comprising an inhomogeneous, uncohesive, solid sheet-like body adhered to the tissue or structure, the body comprising a granular mixture of the chitosan and polysaccharide particles that breaks apart into smaller pieces when peeled away from the surgical site or wound.

The disclosed composition, artificial scab and method are especially useful for tonsillectomy, adenoidectomy and uvulopalatopharyngoplasty (UPPP) procedures.

BRIEF DESCRIPTION OF THE DRAWING

FIG. 1 is a perspective view of a dispenser for the disclosed composition which may be used in the disclosed method. The elements in the drawing are not to scale.

DETAILED DESCRIPTION

The following detailed description describes certain embodiments and is not to be taken in a limiting sense. All amounts, percentages and ratios are by weight, unless otherwise specifically noted. The terms shown below have the following meanings:

The term "airway" means a mammalian breathing passage, e.g., as formed by the mouth, nose, throat and trachea.

The term "antimicrobial" refers to an ability to cause greater than a 90% numeric reduction (viz., at least a 1-log order reduction) in a population of one or more of *Staphylococcus aureus, Pseudomonas aeruginosa, Streptococcus pneumonia, Haemophilus influenzae* or *Moraxella catarrhalis*.

The term "biocompatible" when used in reference to a substance means that the substance presents no significant deleterious or untoward effects upon the body.

The term "biodegradable" when used in reference to a substance means that the substance will degrade or erode in vivo to form smaller chemical or physical species. Such degradation process may be enzymatic, chemical or physical.

The term "bioresorbable" when used in reference to a substance means that the substance is capable of being absorbed by the body.

The term "comminuted" when used in reference to a particulate material means that the particles have been fractured and reduced in size by cutting, grinding, pulverizing, triturating or other particle fracturing process employing externally-applied force.

The term "conformal" when used in reference to a composition applied to a surgical site or wound means that the composition can form a substantially continuous layer over an area to which the composition has been applied.

The term "hemostat" means a device or material which stops blood flow or promotes clotting.

The term "homogeneous" when used in reference to a device or substance means that the device or substance when observed under normal magnification has a substantially uniform composition and physical structure throughout. By way of example, flour, milk and pulpless orange juice are homogenous.

The term "hydratable" when used in reference to a device or substance means that the device or substance can take up water of hydration (viz., chemically-bound water). A "fully hydrated" device or substance is incapable of taking up additional water of hydration. A "partially hydrated" device or substance contains water of hydration and is capable of taking up additional water of hydration.

The term "inhomogeneous" when used in reference to a device or substance means that the device or substance when observed under normal magnification does not have a substantially uniform composition and physical structure throughout. By way of example, date nut bread, chocolate chip ice cream and orange juice with pulp are inhomogeneous.

The term "mucoadhesive" when used in reference to a device or substance means that the device or substance will adhere to the mucus covering epithelia.

The term "nasal or sinus cavities" refers to the various tissues defining the normally air-filled passages and chambers within the nose and sinus including but not limited to the nostrils or nares, the nasal concha or turbinates, the frontal, ethmoid, sphenoid and maxillary sinuses, the sinus ostia and the nasopharnyx.

The term "polysaccharide" includes derivatives of polysaccharides and modified polysaccharides, as well as derivatives of individual polysaccharide species and modified individual polysaccharide species. For example, the term "carboxymethylcellulose" includes carboxymethylcellulose derivatives and modified carboxymethylcelluloses, the term "chitosan" includes chitosan derivatives and modified chitosans, and the term "starch" includes starch derivatives and modified starches.

The term "protective" when used in reference to a material atop a surgical site or wound means that the material may assist in returning a surgically repaired, injured or inflamed tissue surface to a normal state, e.g., through one or more healing mechanisms such as modulation of an inflammatory response, phagocytosis, mucosal remodeling, reciliation or other full or partial restoration of normal function.

The term "residence time" when used in reference to a protective material atop a surgical site or wound means the time period during which the material or portion thereof remains in place in vivo under gross observation.

The term "solvatable" when used in reference to a substance or device means that the substance or device can dissolve or be dissolved in water to form a solution, e.g., by formation or liberation of ions.

The term "substantially collagen-free" means containing a sufficiently low amount of collagen so as not to pose a potential risk of transmission of or infection with bovine spongiform encephalopathy (BSE) or variant Creutzfeldt-Jakob disease (vCJD).

The term "substantially dry" when used in reference to a solvatable powder means the powder contains a sufficiently low amount of water to be free-flowing, for example less than 10% or less than 5% water.

The term "temporary" when used in reference to a protective material atop a surgical site or wound means that the material has a residence time less than one month.

The term "uncohesive" when used in reference to a material on the surface of a surgical site or wound means that the material has a cohesive strength sufficiently less than the mixture's adhesive strength to the surgical site or wound such that the material breaks apart into smaller pieces if peeled away from the surgical site or wound.

Referring to FIG. 1, the disclosed composition may be provided in a bellows-type dispenser 1 which as shown is being held at a downwardly-directed oblique angle by the upward-facing gloved hand 2 of a surgeon, gripped between thumb 4 and first and second fingers 6 and 8. By pressing on the top 10 of bellows 12, powdered artificial scab material 16 can be expelled through straw 18 as a powder stream 20 and applied onto surgical site 22. Removable cap 24 may be used to cover the open end of straw 18. Bellows 12 and straw 18 may be made from a variety of flexible materials, e.g., of translucent polyethylene. When transparent or translucent materials are employed, powder 16 travelling through straw 18 may be visible through the sidewall of straw 18, and the level of powder 16 inside bellows 12 may likewise be visible through the sidewall of bellows 12. Bellows 12 desirably is dimensioned such that it may comfortably be held a user while dispensing a normally desired quantity of powder 16 onto a desired surgical site or wound in an airway. Straw 18 likewise desirably is dimensioned such that it may be held outside a patient's mouth and used to dispense a normally desired quantity of powder 16. Straw 18 may for example be about 120 mm long with a 2 mm ID and a 4 mm OD.

Those skilled in the art will appreciate that the disclosed composition may be applied using methods or devices other than those discussed above. Exemplary other methods include dropping (e.g., sprinkling) the composition into place. Exemplary other devices include spoons, sponges, nebulizers and syringes.

In use, the disclosed composition passes through a series of gages which may be discussed using an A, B, C, D nomenclature. In the first phase, the composition is "Applied" or "Administered" by depositing the disclosed powdered mixture onto a desired surgical site or wound. On the way to the surgical site or wound, substantially dry powder particles may for example travel through the air, and upon landing they desirably tenaciously adhere to tissue and to one another. Adhesion to tissue and to other particles will be aided by the wetting effect of blood and other bodily fluids present in or on the surgical site or wound, or by the wetting effect of water or other fluids added to the surgical site or wound. The powder particles desirably are applied in a relatively thin layer, and if need be with differing thicknesses throughout the layer, but preferably at sufficient thickness to provide complete coverage of the surgical site or wound and a sufficiently robust eventual artificial scab.

In the second phase, the thus-deposited powder undergoes "Bonding" or "Bodily Fluid Solvation" upon becoming at least partially solvated by blood or other bodily fluids. In some cases, e.g., when a surgical site has been thoroughly cauterized and thus is relatively dry, it may be desirable to augment or accelerate solvation by adding a small quantity of water (e.g. as a sterile saline solution) to the surgical site before, during or after powder deposition. The applied particles become adhered both to tissue in the surgical site or wound and to one another. Compared to a hydrogel formed by applying a solution of chitosan and oxidized polysaccharide, or compared to an in situ hydrogel formed by applying separate chitosan and oxidized polysaccharide solutions, the applied dry particles appear to attain increased tissue adhesion. This increase may be due to a delay in the competing inter-particle crosslinking reaction afforded by the application of the chitosan and oxidized polysaccharide as mixed but substantially dry powdered particles rather than as fully solvated species. The degree of initial tissue adhesion desirably is sufficiently high so that the applied powder may be gently irrigated (e.g., using a gravity-fed saline solution dispensed through a cannula or syringe) shortly (e.g., 1 or 2 minutes) after powder application without removing significant quantities of the applied powder from the surgical site or wound. During the Bonding or Bodily Fluid Solvation phase, some degree of hydration may take place. Gel bodies may also form as outer portions of the chitosan or oxidized polysaccharide powder particles become at least partially solvated and at least partially react with one another. Desirably however, the powder particles do not all become fully solvated, viz., do not dissolve to form a uniform solution, and instead retain at least part of the central portion of their original particulate structure in solid, undissolved form. Also, the powder particles desirably do not form a uniform gel and instead retain an inhomogeneous, granular structure containing liquid or gel body regions throughout which are interspersed solid regions. The resulting inhomogeneous structure helps weaken the resulting sheet-like body and assists it in breaking into small pieces rather than coming away from the surgical site or wound as a single large chunk, thereby reducing the risk of aspiration occlusion.

In the third phase, the solvated or partially solvated composition undergoes "Consolidation" or "Crust Formulation" and forms an inhomogeneous, uncohesive (e.g., slightly cohesive), sheet-like solid artificial scab adhered to the surgical site or wound. The rate at which the third phase takes place is assisted by blood clotting, the respiratory cycle, and in many typical surgical sites by their vertical orientation. The resulting artificial scab may have a solid surface and stiffness not present when a hydrogel is formed, and an inhomogeneous surface appearance and inhomogeneous internal structure not present when a uniform polymeric film is formed. The inhomogeneous structure of the artificial scab weakens it and assists the scab in breaking apart into smaller pieces if it is peeled away or otherwise detached from the surgical site or wound. The artificial scab desirably resists detachment or other disruption until natural degradation or resorption takes place. Meanwhile one or more therapeutically desirable benefits provided by natural scabs may be observed including but not limited to hemostasis, improved healing, reduced pain, tissue protection, reduction in inflammation, and reduced formation of adhesions to nearby anatomical structures. The artificial scab may oiler additional, potentially less readily observable advantages including but not limited to bacterial adhesion repellence, anti-infective properties, local immune modulation, optimization of a favorable environment for ciliary regrowth, and the like.

In the fourth stage, the artificial scab undergoes "Disintegration" or "Disappearance" by slowly becoming degraded, resorbed or by breaking apart into small, nonhazardous pieces having minimal risk of aspiration occlusion. This takes place over a residence time in vivo of, for example, from one day to a few (e.g., 2, 3 or 4) days or weeks, and desirably extends past the period during which a typical tonsillectomy patient may experience pain while eating or drinking typical foods or beverages.

A wide variety of solvatable chitosans may be employed in the disclosed composition, artificial scab and method. Chitosan salts including but not limited to citrate, nitrate, lactate, phosphate, chloride and glutamate salts are preferred. Exemplary unmodified chitosans and chitosan salts may be obtained from a variety of commercial sources including Fluka Chemie AG, KitoZyme S.A., Heppe Medical Chitosan GmhH, the NovaMatrix unit of FMC BioPolymer AS and Sigma-Aldrich Co. Chitosan may also be synthesized by deacetylation of chitin (poly-N-acetyl-D-glucosamine) to eliminate acetyl groups on the nitrogen atom by hydrolysis. The resulting polymer has a plurality of repeating units (e.g., about 30 to about 3000 repeating units, about 60 to about 600 repeating units, or such other amount as may be desired for the chosen end use) some or all of which contain deacetylated amino groups (e.g., about 30 to about 100% or about 60 to about 95% of the total repeating units), with the remaining repeating units (if any) containing acetylated amino groups. The polymer is cationic and may be regarded as being composed from glucosamine monomers. The amino groups will react with aldehyde groups present in an oxidized polysaccharide. The chosen chitosan may have a variety of number average molectilar weights, e.g., about 5 to about 2000 kDa, about 10 to about 500 kDa, or about 10 to about 100 kDa. The chitosan may for example be an ultralow molecular weight material having a number average molecular weight less than about 50 kDa, a low molecular weight material having a number average molecular weight of about 50 to about 200 kDa, a medium molecular weight material having a number average molecular weight of about 200 to about 500 kDa or a high molecular weight material having a number average molecular weight greater than about 500 kDa, with high molecular weight materials being preferred. Chitosan derivatives may also be employed, for example derivatives in which one or more hydroxyl or amino groups have been modified for the purpose of altering the solubility or mucoadhesion characteristics of the derivative. Exemplary derivatives include thiolated chitosans, and non-thiolated chitosan derivatives such as acetylated, alkylated or sulfonated chitosans (for example O-alkyl ethers, O-acyl esters, cationized trimethyl chitosans and chitosans modified with polyethylene glycol), Chitosan derivatives may be obtained from a variety of sources. For example, thiolated chitosans may be obtained from ThioMatrix Forschungs Beratungs GmbH and Mucobiomer Biotechnologische Forschungs-und Entwicklungs GmbH or prepared by reaction of chitosan with a suitable thiolated reactant, e.g., as described in published PCT Application No. WO 03/020771 A1, or in Roldo et al., *Mucoadhesive thiolated chitosans as platforms for oral controlled drug delivery: synthesis and in vitro evaluation*, European Journal of Pharmaceutics and Biopharmaceutics, 57, 115-121 (2004), Krauland et al., *Viscoelastic Properties of a New in situ Gelling Thiolated Chitosan Conjugate*, Drug Development And Industrial Pharmacy, 31, 885-893 (2005), Bernkop-Schnürch, *Thiomers: A new generation of mucoadhesive polymers*, Advanced Drug Delivery Reviews, 57, 1569-1582 Schnürch et al., *Thiomers: Preparation and in vitro*

*evaluation of a mucoadhesive nonoparticulate drug delivery system*, International journal of Pharmaceutics,76-81 (2006) and Weng et al., *Rhealogical Characterizatian of in Situ Crosslinkable Hydrogels Formulated from Oxidized Dextran and N-Carboxyethyl Chitosan*, Biomacromolecules, 8, 1109-1115 (2007).

A wide variety of oxidized polysaccharides may be employed in the disclosed composition, artificial scab and method. Exemplary polysaccharides include agars, alginates, carrageenans, celluloses, chitins, chitosans (thus enabling chitosan to be crosslinked using its oxidized counterpart), chondroitin sulfates, dextrans, galactomannans, glycogens, hyaluronic acids, starches and other biocompatible polysaccharides capable of being oxidized. Oxidized polysaccharides such as oxidized cellulose chitin, chitosan chondroitin sulfate, dextran, glycogen, hyaluronic acid and starch are preferred, and oxidized starch is particularly preferred. The polysaccharide desirably is oxidized to an extent sufficient to provide aldehyde groups capable of promoting information of the disclosed inhomogeneous, uncohesive temporary artificial scab. Representative oxidizing agents or techniques include the use of a) sodium periodate, b) hypochlorite ion in the presence of di-tert-alkylnitroxyl catalysts, c) metal-catalyzed oxidation, using for example ruthenium, d) anhydrous oxidation using for example nitrogen dioxide in for example a halocarbon, e) enzymatic or chemo-enzymatic oxidation of starch, guar and other polysaccharides, and other oxidation agents and techniques that will be known to persons having ordinary skill in the art. Depending on the selected oxidizing agent or technique, a variety of degrees of oxidation, degrees of polymerization and oxidation sites may be employed. For example, oxidation may be directed at a primary hydroxyl group (for example, the 6-hydroxyl group in the anhydroglucose units of glucans), resulting in carboxyl-polysaccharides with preserved ring structures. Oxidation may also be directed at a vicinal diol function present in a monosaccharide ring (for example, the C2-C3 site in anhydroglucose units), resulting in cleavage of the monosaccharide unites and the production of dialdehyde or dicarboxyl functional groups. The dialdehyde content of such an oxidized polysaccharide may range from a degree of oxidation of, for example, 2% to virtually 100%, e.g., more than 30% or more than 50% of the available oxidation sites. The oxidized polysaccharide may also contain other functional groups, for example hydroxyalkyl groups, cationic groups, carboxyl groups and other acid groups. As a generalization, reduced amounts of oxidized polysaccharide may be employed in the disclosed composition, artificial scab and method as the degree of polysaccharide oxidation is increased. Exemplary oxidized polysaccharides may be obtained from a variety of commercial sources including CarboMer Inc., Monomer-Polymer and Dajac Labs, Inc. and Sigma-Aldrich Co.

Both the chitosan and oxidized polysaccharide desirably are obtained in dry particulate form, for example, as free-flowing granules whose average particle diameter is less than about 1 mm, less than about 100 μm, about 1 to about 80 μm, or less than 1 μm. Either or both of the chitosan and oxidized polysaccharide may be conuninuted, lyophilized or crystalline if desired. The chitosan and oxidized polysaccharide desirably are intimately mixed together prior to shipment to end users, so that no mixing is required at the point of use. Recommended chitosan and oxidized polysaccharide amounts in the resulting powdered mixture typically will depend on the respective chitosan and oxidized polysaccharide functionalities and molecular weights, for example based on the degree of oxidation of the oxidized polysaccharide(s). As a generalization, lower oxidized polysaccharide amounts may be used when more highly-oxidized polysaccharides are employed. For some applications the chitosan amount will preferably be as high as may be feasible in order to provide good antimicrobial properties, and in such cases it will be preferable to use a low amount of highly oxidized polysaccharide so as to obtain rapid artificial scab formation. The chitosan and oxidized polysaccharide may each for example be about 10 to about 90%, about 20 to about 80% or about 30 to about 70% of the powdered mixture. Expressed as a ratio, the chitosan and oxidized polysaccharide may for example be combined in a ratio of about 10:1 to about 1:20, about 5:1 to about 1:10, or about 3:1 to about 1:5.

Compared to crosslinking using a low molecular weight aldehyde such as glutaraldehyde or genipin, oxidized polysaccharides appear to provide faster artificial scab formation while avoiding the use of liquid low molecular weight aldehydes. In addition to their ability to react with amine groups in the chitosan, aldehyde groups in the oxidized polysaccharide may also enhance mucoadhesion. The oxidized polysaccharides may provide additional benefits including improved or better controlled biodegradability, bioresorbability, drug delivery or hemostatic properties. The presence of phosphate ions appears to accelerate the crosslinking reaction. Phosphate may be provided by adding an appropriate powdered phosphate to the chitosan/oxidized polysaccharide powder mixture.

The disclosed compositions desirably are substantially collagen-free. Preferably the compositions are sufficiently free of collagen (e.g., containing no collagen at all) so as to be saleable worldwide for use without restriction in humans.

The disclosed compositions may optionally include a variety of other dry ingredients. Exemplary other ingredients include suitable acids, bases, buffering agents, antimicrobial agents, therapeutic agents and other adjuvants. An acid, base or buffering agent may for example help maintain the composition at an appropriate pH for contacting human tissue, e.g., a pH greater than 5, a near-neutral pH, or a pH less than 8.5. Exemplary buffering agents include barbitone sodium, glycinamide, glycine, potassium chloride, potassium phosphate, potassium hydrogen phthalate, sodium acetate, sodium citrate, sodium phosphate and their conjugate acids.

The disclosed compositions desirably are inherently antimicrobial without requiring addition of a separate antimicrobial agent. Antimicrobial activity may be influenced by the proportion of chitosan in the composition (with higher chitosan proportions tending to provide greater antimicrobial activity) and by the number of available chitosan amine hydrogen atoms. Accordingly, use of chitosan derivatives containing low numbers of available amino hydrogen atoms (such as the N-carboxyethyl derivatives desired in the above-mentioned Weng et al. paper) may be contraindicated. In any event, a separate antimicrobial agent may be employed if desired. A useful list of such antimicrobial agents may be found, for example, in U.S. Patent Application Publication No. US 2007/0264310 A1 .

Exemplary therapeutic agents which may be employed in the disclosed compositions include any material suitable for use at the intended treatment site including analgesics, anti-cholinergics, anti-fungal agents, antihistamines, steroidal or non-steroidal anti-inflammatory agents, anti-parasitic agents, antiviral agents, biostatic compositions, chemotherapeutic/antineoplastie agents, cytokines, decongestants, additional hemostatic agents beyond those already provided by the disclosed powdered mixture itself (e.g., thrombin), immunosuppressors, mucolytics, nucleic acids, peptides, proteins, steroids, vasoconstrictors, vitamins, mixtures thereof, and other therapeutic materials that will be known to those skilled in the art. A useful list of such therapeutic agents may be found, for example, in the above-mentioned U.S. Patent Application Publication No. US 2007/0264310 A1.

Other adjuvants that may be included in the disclosed compositions include dyes, pigments or other colorants (e.g., FD & C Red No. 3, FD & C Red No. 20, FD & C Yellow No, 6, FD & C Blue No. 2, D & C Green No. 5, D & C Orange No. 4, D & C Red No. 8, caramel, titanium dioxide, fruit or vegetable colorants such as beet powder or beta-carotene, turmeric, paprika and other materials that will be known to those skilled in the art); indicators; flavoring or sweetening agents including but not limited to anise oil, cherry, cinnamon oil, citrus oil (e.g., lemon, lime or orange oil ), cocoa, eucalyptus herbal aromatics (e.g., clove oil, sage oil or cassia oil), lactose, maltose, menthol, peppermint oil, saccharine, sodium cyclamate, spearmint oil, sorbitol, sucrose, vanillin, wintergreen oil, xylitol and mixtures thereof; antioxidants and antifoam agents. The disclosed compositions desirably do not contain ingredients which might potentially harm mucosal tissues or structures.

In those instances where it is desirable to remove water from tissue, e.g., to remove fluid from polyps or edematous tissue, a hyperosmolar agent may be employed in the disclosed compositions. Exemplary hyperosmolar agents include furosemide, sodium chloride and other salts that draw water from tissue. Where sustained release or delayed release of a therapeutic agent is desirable, a release agent modifier may also be included.

The disclosed composition typically will be subjected to sterilization and placed in suitable sealed packaging prior to shipment to an end user. Additional property customization may be carried out by using a sterilization procedure such as gamma radiation or electron beam (E-Beam.) processing to cause controlled chain scission. Cold ionizing radiation sterilization (e.g., cold E-Beam sterilization) may be employed to limit the degree of chain scission, as discussed in established PCT Application No. WO 2009/132229 A2.

The invention is further illustrated in the following non-limiting examples.

EXAMPLE 1

A powder blend was prepared from a 50:50 mixture of chitosan glutamate (PROTASAN™ UP G 213 from the NovaMatrix unit of FMC BioPolymer AS) and oxidized starch (P9265 polymeric dialdehyde from Sigma-Aldrich). The blend, identified below as Run No. 1, was evaluated for in vivo mucoadhesion using a Hamster cheek pouch model in which two sites on each cheek pouch were everted using sandpaper, followed by application of the test sample to the exposed surface. The animals were collared to prevent expelling the sample, and residence time was evaluated by visual inspection at 1, 3, 5 and 7 days after placement. The powder blend was also applied to a piece of moist sausage casing and subjectively evaluated by a panel of physicians to assess the risk of airway occlusion as the blend aged. Similar mucoadhesion and airway occlusion evaluations were performed on a sample (Run No. 2) made using Dialdehyde Starch 9056 from Monomer-Polymer and Dajac Labs, Inc. as the oxidized starch, cold e-beam sterilized as described in published PCT Application No. WO 2009/132229 A2. Seven other commercially or experimentally available sealants (Run Nos. 3 through 9), were similarly evaluated. The results are shown below:

TABLE 1

| Run No. | Material | Supplier | Residence Time | Risk of Air Occlusion? |
|---|---|---|---|---|
| 1 | Chitosan Glutamate/Oxidized Starch Powder Blend | — | 4 of 6 sites at day 7 | No |
| 2 | Cold E-Beam sterilized Chitosan Glutamate/Oxidized Starch Powder Blend | — | 4 of 4 sites at day 7 | no |
| 3 | CT3 ™ polyethylene glycol/collagen sealant | AngioTech Pharmaceuticals | 0 sites adhered at any time | Not Evaluated |
| 4 | DERMABOND ™ Liquid Bonding Agent (an octyl cyanoacrylate) | Ethicon, Inc. | 1 of 4 sites at day 7 | yes |
| 5 | derma + flex QS ™ 2-octyl cyanoacrylate | Chemence Medical Products, Inc. | 0 of 4 sites at day 3 | yes |
| 6 | HENKEL ™ 2-butyl cyanoacrylate | Henkel Corporation | 1 of 4 sites at day 5 | yes |
| 7 | MEDHESIVE-E ™ (adhesive derived from mollusks) | Nerites Corporation | 1 of 4 sites at day 7 | yes |
| 8 | PPTI ™ silk elastin/ polyethylene glycol sealant | Protein Polymer Technologies, Inc. | 0 sites adhered at any time | Not Evaluated |
| 9 | SANGUIBOND tissue sealant (a bovine serum albumin/glutaraldehyde blend) | Southeastern Medical Technologies | 1 of 4 sites at day 7 | yes |

The results in Table 1 show that the Run No. 1 and Run No. 2 materials provided much better residence time than the other tested materials and in the opinion of the evaluating physicians did not pose an air occlusion risk. Sites treated with the Run No. 1 and Run No. 2 materials also had a significantly different initial appearance than sites treated with the other tested materials. Sites treated with the Run No. 1 and Run No. 2 materials looked like a thin but generally continuous layer of table salt had been poured over the site, whereas sites treated with the other materials had a translucent or transparent liquid covering. It was very easy to determine where the Run No. 1 and Run No. 2 materials had been applied and to assess the degree of coverage and initial powder solvation.

EXAMPLE 2

The Example 1, Run 1 powder blend was evaluated using a canine tonsillectomy model and found via histologic analysis to be a non-irritant compared to an untreated control. A second canine tonsillectomy study was performed to assess bleeding control using various electrocautery excision settings and an irrigation step performed shortly after powder application. The powder blend was found to adhere well and to control bleeding in all sites without regard to the electrocautery setting. The applied powder blend remained in place even after being irrigated. Tonsillar bed healing was also examined, and the results showed that the lower the electrocautery setting, the better was the observed healing.

EXAMPLE 3

The Example 1, Run No. 1 powder blend was evaluated in a Swine Liver Biopsy Punch Hemostasis Model. The blend qualified as hemostatic, with performance similar to that provided by HemCon™ Bandage from HemCon Medical Technologies, Inc., which is a chitosan-based hemostatic material on a flexible backing.

EXAMPLE 4

A third canine tonsillectomy study was performed to assess healing efficacy. Ten days after application, wound sites treated with the Example 1, Run No. 2 powder blend were approximately 50% smaller than untreated control sites.

Based on the studies performed and the associated data, the chitosan/oxidized polysaccharide powder blend adhered well to wound sites, provided intra-operative hemostasis and provided improved wound healing. The blend also appeared to be a non-irritant, to be adhesive to mucosa but not cohesive to itself, and was not an occlusive risk.

Although specific embodiments have been illustrated and described herein for purposes of description of the preferred embodiments, it will be appreciated by those of ordinary skill in the art that a wide variety of alternate or equivalent implementations calculated to achieve the same purposes may be substituted for the specific embodiments shown and described without departing from the scope of the present invention. This application is intended to cover any adaptations or variations of the preferred embodiments discussed herein. Therefore, it is manifestly intended that this invention be limited only by the claims and the equivalents thereof.

The invention claimed is:

1. A method comprising:
a) applying a substantially dry, free-flowing powdered mixture of about 10 to about 90 wt. % at least partially solvatable chitosan particles containing amino groups and about 90 to about 10 wt. % at least partially solvatable oxidized polysaccharide particles containing aldehyde groups to tissue or structure in a surgical site or wound in an airway moistened with blood, other bodily fluids or water, wherein substantially dry means the powder contains less than 10 wt. % water, and wherein the amino group functionality and molecular weight of the chitosan and the aldehyde group functionality and molecular weight of the oxidized polysaccharide are such that the particles adhere to such site or wound and to one another by inter-particle cross-linking reaction of amino groups on the chitosan particles with aldehyde groups on the polysaccharide particles, thereby
b) forming an artificial scab comprising an inhomogeneous, uncohesive, solid sheet-like body adhered to the tissue or structure, the body comprising a granular mixture of the chitosan and polysaccharide particles that breaks apart into smaller pieces when peeled away from the surgical site or wound.

2. A method according to claim 1 wherein the substantially dry, free-flowing powdered mixture contains less than 5 wt. % water.

3. A method according to claim 1 wherein upon application of the mixture to the surgical site or wound the chitosan particles and polysaccharide particles become at least partially solvated and at least partially react with one another.

4. A method according to claim 1 wherein upon application of the mixture to the surgical site or wound the chitosan particles and polysaccharide particles do not all become fully solvated, and instead retain at least part of the central portion of their original particulate structure in solid, undissolved form.

5. A method according to claim 1 further comprising irrigating the applied powdered mixture without removing significant quantities of the applied powder from the surgical site or wound.

6. A method according to claim 1 wherein the solid sheet-like body is not a hydrogel, and is not a translucent or transparent liquid covering.

7. A method according to claim 1 wherein the surgical site comprises a tonsillectomy site.

8. A method according to claim 1 wherein the solid sheet-like body has a residence time greater than 3 days.

9. A method according to claim 1 wherein the solid sheet-like body has a residence time less than 2 weeks.

10. A method according to claim 1 wherein the chitosan comprises a high molecular weight chitosan.

11. A method according to claim 1 wherein the chitosan comprises a salt.

12. A method according to claim 1 wherein the chitosan comprises a glutamate salt.

13. A method according to claim 1 wherein the oxidized polysaccharide comprises oxidized cellulose, chitin, chitosan, chondroitin sulfate, dextran, glycogen or hyaluronic acid.

14. A method according to claim 1 wherein the oxidized polysaccharide comprises oxidized starch.

15. A method according to claim 1 wherein the mixture contains about 30 to about 70 wt. % chitosan and about 70 to about 30 wt. % oxidized polysaccharide.

16. A method according to claim 1 wherein the mixture contains an antimicrobial agent.

17. A method according to claim 1 wherein the mixture contains an analgesic, anti-cholinergic, anti-fungal agent, antihistamine, steroidal or non-steroidal anti-inflammatory agent, anti-parasitic agent, antiviral agent, biostatic composition, chemotherapeutic or antineoplastic agent, cytokine, decongestant, additional hemostatic agent, immunosuppressor, mucolytic, nucleic acid, peptide, protein, steroid, vasoconstrictor, vitamin or mixture thereof.

18. A method according to claim 1 wherein the powdered mixture is sterilized and is provided in sealed packaging.

* * * * *